United States Patent

Witek et al.

[11] 4,217,365
[45] Aug. 12, 1980

[54] FUNGICIDAL QUATERNARY AMMONIUM COMPOSITION

[76] Inventors: Stanislaw Witek, Swobodna Str., 12, Wroclaw; Damian Grobelny, Cieszkowskiego Str., 15, Wroclaw; Janina Ptaszkowska, Ks. Janusza Str., 62, Warszawa; Andrzej Bielecki, R. Luksemburg Str., 25, Opole; Edmund Bakuniak, Dzielna Str., 11a, Warszawa; Stefan Fulde, Traugutta Str., 7/9, Warszawa; Jadwiga Gorska-Poczopko, Instytucka Str., 4, Jablonna/k Warszawy, all of Poland

[21] Appl. No.: 884,842

[22] Filed: Mar. 9, 1978

[30] Foreign Application Priority Data

Mar. 11, 1977 [PL] Poland .................................. 196612

[51] Int. Cl.$^2$ .............................................. A01N 9/20
[52] U.S. Cl. ...................... 424/329; 424/267; 424/248.56; 544/162; 546/232; 260/567.6 M
[58] Field of Search ............... 424/329; 260/567.6 M

[56] References Cited

U.S. PATENT DOCUMENTS 3,419,562  12/1968  Wakeman et al. ................... 424/329

FOREIGN PATENT DOCUMENTS 587240  11/1959  Canada ............................. 260/567.6 M Primary Examiner—Henry R. Jiles
Assistant Examiner—Robert T. Bond

[57] ABSTRACT

A parasiticide containing as an active ingredient the compound with the general formula

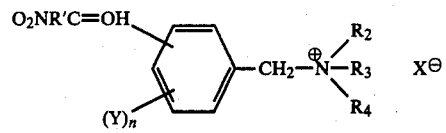

where:
X is a halogen atom,
Y is a hydroxyl, alkoxyl, alkyl or nitro group and "n" is the number of Y substituents and equals 0–4,
$R^1$ is an alkyl radical with 1–3 carbon atoms or hydrogen atom,
$R^2$ and $R^3$ are alkyl or hydroxyalkyl radicals with 1–4 carbon atoms,
$R^4$ is an alkyl radical with 1–18 carbon atoms or $R^2$ and $R^3$ together with the nitrogen atom form a ring substituted as in formula

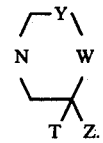

where:
W is a methylene group or an oxygen atom,
U and T are methyl radicals or hydrogen atoms,
Z is a hydrogen atom or T and Z together are an oxygen atom.

The agent containing an active compound with the general formula 1, where the substituents have the above meaning has strong fungicidal activity towards pathogenic fungi and bacteria, among which are fungi from the Alternaria genus.

6 Claims, No Drawings

FUNGICIDAL QUATERNARY AMMONIUM COMPOSITION

This invention relates to a composition containing new active agents, for control of pathogens causing plant diseases.

A variety of substances is known for control of pathogens causing plant diseases.

Among others, fungicides from the benzimidazole group are commonly used. However, it has been stated that repeated application of these effective, though very selective, fungicides causes changes in plant parasite microflora. Pathogens destroyed by benzimidazole derivatives are replaced by others, such as fungi from the Alternaria genus, giving rise to difficulty controlled plant diseases.

Unexpectedly, it has been found that undescribed until now substances with the general formula 1, where:
X is a halogen atom,
Y is a hydroxyl, alkoxyl, alkyl or nitro group and "n" is the number of Y substituents, and equals 0-4,
$R^1$ is an alkyl radical with 1-3 carbon atoms or a hydrogen atom,
$R^2$ and $R^3$ are alkyl or hydroxyalkyl radicals with 1-4 carbon atoms,
$R^4$ is an alkyl radical with 1-18 carbon atoms,
or
$R^2$ and $R^3$ together with the nitrogen atom form a ring substituted as in formula 2, where:
W is a methylene group or an oxygen atom,
U and T are methyl radicals or hydrogen atoms,
Z is a hydrogen atom,
or
T and Z together are an oxygen atom,

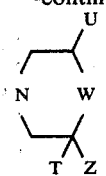

exhibit strong activity towards pathogens causing plant diseases.

The composition according to the present invention, containing an active compound with the general formula 1, where the substituents have the above meaning, have strong fungicidal activity towards pathogenic fungi and bacteria, among which are fungi from the Alternaria genus.

Effectiveness of the composition according to the present invention towards the Alternaria, Botrytis, Rhizoctonia, Fusarium and Aspergillus genera was tested in comparison to known fungicides, such as carbendazime/2-benzimidazole-carbamic acid methyl ester/, methylthiophanate/1,2-bis/3-methoxy-carbonyl-2-thioureido/-benzene/and tridemorph/N-tridecyl-2,6-dimethylmorpholine/.

Effectiveness of compounds with the general formula 3 was tested in vitro on Alternaria tenuis spores from a 4-day culture and Botrytis cinerea spores from a 14-day culture. Results of investgations are given in table 1. As a measure of effectiveness was taken the lowest concentration, completely inhibiting spore germination.

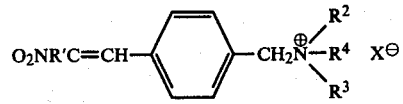

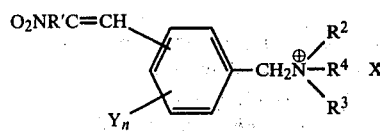

Table 1

Effectiveness of compounds with the general formula 3.

| No | $R^1$ | $R^2$ | $R^3$ | $R^4$ | X | Alternaria tenuis (ppm) | Botrytis cinerea (ppm) |
|---|---|---|---|---|---|---|---|
| 1 | —CH$_3$ | —CH$_3$ | —CH$_3$ | —C$_8$H$_{17}$ | Br | >1000 | 1000 |
| 2 | —CH$_3$ | —CH$_3$ | —CH$_3$ | —C$_{10}$H$_{21}$ | Cl | ±1000 | 100 |
| 3 | —CH$_3$ | —CH$_3$ | —CH$_3$ | —C$_{12}$H$_{25}$ | Cl | 100 | <10>1 |
| 4 | —CH$_3$ | —CH$_3$ | —CH$_2$—CH$_2$OH | —C$_{10}$H$_{21}$ | Cl | 100 | 100 |
| 5 | —CH$_3$ | —CH$_3$ | —CH$_2$CH$_2$OH | —C$_{12}$H$_{25}$ | Cl | 100 | <10>1 |
| 6 | —CH$_3$ | —CH$_2$CH$_2$O—CH$_2$CH$_2$— | | —C$_7$H$_{15}$ | J | >1000 | ±100 |
| 7 | —CH$_3$ | —CH$_2$CH$_2$—O—CH$_2$CH$_2$— | | —C$_7$H$_{15}$ | Cl | 1000 | 100 |
| 8 | —CH$_3$ | —CH$_2$CH$_2$—O—CH$_2$CH$_2$— | | —C$_8$H$_{17}$ | Cl | ±100 | 100 |
| 9 | —CH$_3$ | —CH$_2$CH$_2$—O—CH$_2$CH$_2$— | | —C$_{10}$H$_{21}$ | Cl | 100 | 100 |
| 10 | —CH$_3$ | —CH$_2$CH$_2$—O—CH$_2$CH$_2$— | | —C$_{12}$H$_{25}$ | Cl | 100 | ±10 |
| 11 | —CH$_3$ | —CH$_2$CH$_2$—O—CH$_2$CH$_2$— | | —C$_{14}$H$_{29}$ | Cl | 10 | <10>1 |
| 12 | —CH$_3$ | —CH$_2$CH—O—CH—CH$_2$ (CH$_3$, CH$_3$) | | —C$_{12}$H$_{25}$ | Cl | 100 | <10>1 |
| Carbendazime | | | | | | >1000 | ±10 |
| Methylthiophanate | | | | | | >1000 | ±10 |
| Tridemorph | | | | | | >1000 | >1000 |

Germination of Alternaria tenuis spores was inhibited in concentrations of the compounds significantly lower than concentrations of reference fungicides: carbendazime, methylthiophanate, tridemorph. Especially effective was compound 11, which inhibited spore germination in concentrations 100 times lower than the known fungicides.

Germination of Botrytis cinerea spores was inhibited by lower concentrations of compounds 3, 5, 11, 12 and equal concentrations of compound 10 compared to carbendazime and methylthiophanate and in 100 times lower concentrations compared to tridemorph.

Effectiveness of compounds with the general formula 4 was tested similarly as for compounds with the general formula 3.

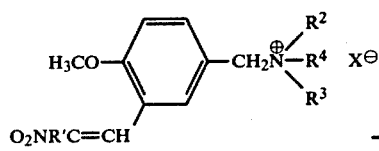
(4)

Effectiveness of compounds with the general formula 5 was tested similarly as for compounds with the general formula 3.

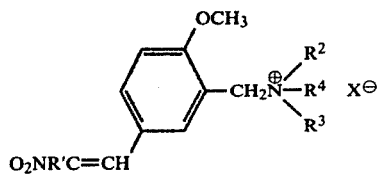
(5)

Results are given in table 3.

Table 3

| | Effectiveness of compounds with the general formula 5. | | | | | | |
|---|---|---|---|---|---|---|---|
| | | | | | | Concentration inhibiting germination of spores in ppm | |
| No | $R^1$ | $R^2$ | $R^3$ | $R^4$ | X | Alternaria tenuis | Botrytis cinerea |
| 26 | —$CH_3$ | —$CH_3$ | —$CH_3$ | —$C_7H_{15}$ | Br | 1000 | ±100 |
| 27 | —$CH_3$ | —$CH_3$ | —$CH_3$ | —$C_{10}H_{21}$ | Cl | ±100 | 100 |
| 28 | —$CH_3$ | —$CH_3$ | —$CH_3$ | —$C_{12}H_{25}$ | Cl | ±10 | <10>1 |
| 29 | —$CH_3$ | —$CH_3$ | —$CH_2CH_2OH$ | —$C_8H_{17}$ | Cl | ±100 | 1000 |
| 30 | —$CH_3$ | —$CH_3$ | —$CH_2CH_2OH$ | —$C_{10}H_{21}$ | Cl | ±1000 | ±10 |
| 31 | —$CH_3$ | —$CH_3$ | —$CH_2CH_2OH$ | —$C_{12}H_{25}$ | Cl | ±100 | <10>1 |
| 32 | —$CH_3$ | —$C_2H_5$ | —$CH_2CH_2OH$ | —$C_{10}H_{21}$ | Cl | 10 | ±10 |
| 33 | —$CH_3$ | —$C_2H_5$ | —$CH_2CH_2OH$ | —$C_{12}H_{25}$ | Cl | <10>1 | <10>1 |
| 34 | —$CH_3$ | —$CH_2$—$CH_2$—O—$CH_2CH_2$— | | —$C_7H_{15}$ | J | >1000 | ±1000 |
| 35 | —$CH_3$ | —$CH_2CH_2$—O—$CH_2CH_2$— | | —$C_7H_{15}$ | Cl | >1000 | 1000 |
| 36 | —$CH_3$ | —$CH_2CH_2$—O—$CH_2CH_2$— | | —$C_8H_{17}$ | Cl | 100 | <10>1 |
| 37 | —$CH_3$ | —$CH_2CH_2$—O—$CH_2CH_2$— | | —$C_{10}H_{21}$ | Cl | ±100 | <10>1 |
| 38 | —$CH_3$ | —$CH_2CH_2$—O—$CH_2CH_2$— | | —$C_{12}H_{25}$ | Cl | 100 | <10>1 |
| 39 | —$CH_3$ | —$CH_2CH$—O—$CHCH_2$— $\phantom{xx}$ \| $\phantom{xxxxxx}$ \| $\phantom{xxxx}$ $CH_3$ $\phantom{xxxx}$ $CH_3$ | | —$C_{12}H_{25}$ | Cl | 100 | <10>1 |
| Carbendazime | | | | | | >1000 | ±10 |
| Methylthiophanate | | | | | | >1000 | ±10 |
| Tridemorph | | | | | | >1000 | >1000 |

Results are given in table 2.

Table 2

| | Effectiveness of compounds with the general formula 4. | | | | | |
|---|---|---|---|---|---|---|
| | | | | | Concentration inhibiting spore germination in ppm | |
| No | $R^1$ | $R^2$ | $R^3$ | $R^4$ | X | Alternaria tenuis | Botrytis cinerea |
| 13 | —$CH_3$ | —$CH_3$ | —$CH_3$ | —$C_8H_{17}$ | Br | >1000 | ±100 |
| 14 | —H | —$CH_3$ | —$CH_3$ | —$C_{10}H_{21}$ | Cl | 100 | <10>1 |
| 15 | —$CH_3$ | —$CH_3$ | —$CH_3$ | —$C_{10}H_{21}$ | Cl | ±1000 | <10>1 |
| 16 | —$CH_3$ | —$CH_3$ | —$CH_3$ | —$C_{12}H_{25}$ | Cl | 100 | <10>1 |
| 17 | —$CH_3$ | —$CH_3$ | —$CH_2CH_2OH$ | —$C_{10}H_{21}$ | Cl | ±10 | <10>1 |
| 18 | —H | —$CH_3$ | —$CH_2CH_2OH$ | —$C_{12}H_{25}$ | Cl | ±10 | <10>1 |
| 19 | —$CH_3$ | —$C_2H_5$ | —$CH_2CH_2OH$ | —$C_{12}H_{25}$ | Cl | ±10 | ±10 |
| 20 | —$CH_3$—$CH_2CH_2$—O—$CH_2CH_2$— | | | —$C_7H_{15}$ | Cl | 1000 | <10>1 |
| 21 | —$CH_3$—$CH_2CH_2$—O—$CH_2CH_2$— | | | —$C_8H_{17}$ | Cl | 100 | <10>1 |
| 22 | —$CH_3$—$CH_2CH_2$—O—$CH_2CH_2$— | | | —$C_{10}H_{21}$ | Cl | 100 | <10>1 |
| 23 | —$CH_3$—$CH_2CH_2$—O—$CH_2CH_2$— | | | —$C_{12}H_{25}$ | Cl | <10>1 | <10>1 |
| 24 | —$CH_3$—$CH_2CH_2$—O—$CH_2CH_2$— | | | —$C_{14}H_{29}$ | Cl | <10>1 | ±10 |
| 25 | —$CH_3$—$CH_2CH_2$—O—$CH_2CH_2$— | | | —$C_{16}H_{33}$ | Cl | ±10 | ±10 |
| Carbendazime | | | | | | >1000 | ±10 |
| Methylthiophanate | | | | | | >1000 | ±10 |
| Tridemorph | | | | | | >1000 | >1000 |

Compounds 17, 18, 19, 24 and 25 were much more effective towards Alternaria tenuis than the reference fungicides. For Botrytis cinerea, most of the compounds were more effective than the reference fungicides.

Most of the tested compounds were more effective towards Alternaria tenuis than the reference fungicides. Especially effective was compound No. 32. Most of the tested compounds were more effective towards Botrytis cinerea than the reference fungicides.

Compounds described by the general formula 1 may be prepared by quarternation from $R^2$, $R^3$, $R^4N$ tertiary amines, where $R^2$, $R^3$ and $R^4$ have the above meaning, with appropriately substituted halogen methyl-$\beta$-nitro- β-alkyl styrenes or halogen methyl-β-nitro styrenes. Quarternation may be carried out in solution with solvents such as benzene, acetone, dimethylformamide or their mixtures. Most of the tertiary amines were prepared through alkylation of secondary amines by known methods; derivatives of 2-oxo-morpholine were obtained by alkylation and cyclization reactions of appropriate monoalkyl ethanolamines with chloracetic acid esters.

Compounds described by formula 1 may also be prepared by quaternation of appropriate N,N-dialkyl-/β-nitroalkenyl/-benzylamines with alkyl halides. Compounds with the general formula 1 have typical chemical properties of quaternary ammonium salts and are soluble in water; thus their application is simplified.

The composition according to the present invention may be used as water solutions, wettable powders, concentrated powders for dusting, emulsions, pastes and tablets. To achieve this, the biologically active substance is mixed with appropriate mineral or organic carriers such as kaolin, synthetic or natural kieselguhr, bentonite, talc, grain flour, woodbark or walnut shell flour; thinners or solvents as water, methanol, ethanol, ethyleneglycol and surface-active agents, emulsifiers, dispersers and wetting agents as ammonium salts, alkali or alkaline earth metal salts, lignine sulphonic acids, alkyl or aryl sulphonic acids, alkyl or aryl sulphonic derivatives, derivatives of N-methyl-taurine or adducts of ethylene oxide to fatty alcohols, fatty acids or higher aromatic or aliphatic amines.

The final product may contain other additives, such as buffers, densifiers, adherents, antifoaming agents and colors.

The compositions according to the present invention may be introduced into molded materials for encapsulation of seeds prepared for sowing. They may also be used as an additive for paints, lacquers and other polymers for protection against destructive fungi.

An advantage of the compositions according to the present invention is the simplicity of their application arising from solubility of the active compounds in water, along with higher effectiveness of some compounds in comparison to known and presently used fungicides. Good solubility in water simplifies assimilation by plants and enables systemic activity. Another advantage of the compositions is their broad spectrum of activity towards pathogens, with effective inhibitive activity towards some bacteria. Example I. 10 parts by weight of N-dodecyl-N-ethyl-N-/2-hydroxyethyl/-N-[2-methoxy-5-/β-nitro-β-methyl-vinyl/benzyl] amine chloride were mixed with 0,3 part by weight of alkylarylpolyglycol ether and 89,7 parts by weight of distilled water.

This composition, in liquid form, tested in concentrations of the active compound from 1 to 10 ppm, very effectively inhibited germination of Alternaris tenuis and Botrytis cinerea spores. Example II. 50 parts by weight of N-dodecyl-N-[3-/β-nitro-β-methyl-vinyl/-4-methoxy-benzyl] morpholine chloride were mixed with 40% of mineral carrier/kieselguhr/, 2% of wetting agent+8% disperser/waste calcium sulphite liquor/.

The resulting wettable powder, dissolved in water to obtain active compound concentrations of 1-10 ppm completely inhibited germination of Alternaris tenuis and Botrytis cinerea spores.

We claim:

1. A fungicidal composition containing as the active substance therein a fungicidally effective amount of a compound having the general formula

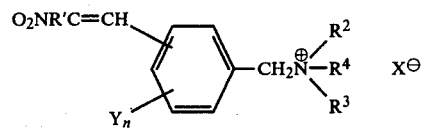

wherein
$R^1$ is an alkyl radical containing 1–3 carbon atoms or a hydrogen atom,
x is a halogen atom,
$R^2$ and $R^3$ are alkyl or hydroxyalkyl radicals containing 1–4 carbon atoms,
$R^4$ is an alkyl radical containing 1–18 carbon atoms,
y is a hydroxyl, lower alkoxyl, alkyl or nitro group, and
n is the number of y substituents and equals 0–4, and a mineral or organic carrier.

2. A fungicidal composition of claim 1, wherein said compound is N-dodecyl-N-ethyl N-2-hydroxy-ethyl N-2-methoxy-5-(β-nitro-β-methyl-vinyl)benzyl amine chloride.

3. A fungicidal composition of claim 1, wherein said compound is N-decyl N-methyl N-2-hydroxyethyl N-3-methoxy-4-(β-nitro-β-methyl-vinyl)benzyl amine chloride.

4. A fungicidal composition of claim 1, wherein said compound is N-dodecyl N-ethyl N-2-hydroxy-ethyl N-3-methoxy-4-(β-nitro-β-methyl-vinyl)benzyl amine chloride.

5. A fungicidal composition of claim 1, wherein said compound is N-dodecyl n-dimethyl N-2-methoxy-5-(β-nitro-β-methyl-vinyl) benzyl amine chloride.

6. A fungicidal composition of claim 1, wherein said compound is N-decyl N-ethyl N-2-hydroxyethyl N-2-methoxy-5-(β-nitro-β-methyl-vinyl)benzyl amine chloride.

* * * * *